(12) United States Patent     (10) Patent No.:   US 12,638,123 B2

Høiland     (45) Date of Patent:    May 26, 2026

---

(54) METHOD AND A SYSTEM FOR REDUCING CORROSIVE ENVIRONMENT FOR A PIPELINE

(71) Applicant: Nitrogas AS, Stavanger (NO)

(72) Inventor: Geir Magne Høiland, Sandnes (NO)

(73) Assignee: Nitrogas AS, Stavanger (NO)

( * ) Notice: Subject to any disclaimer, the term of this patent is extended or adjusted under 35 U.S.C. 154(b) by 51 days.

(21) Appl. No.: 18/712,022

(22) PCT Filed: Dec. 5, 2022

(86) PCT No.: PCT/NO2022/050277

§ 371 (c)(1),
(2) Date: May 21, 2024

(87) PCT Pub. No.: WO2023/106925

PCT Pub. Date: Jun. 15, 2023

(65) Prior Publication Data

US 2025/0012397 A1     Jan. 9, 2025

(30) Foreign Application Priority Data

Dec. 8, 2021    (NO) ................................... 20211477

(51) Int. Cl.
    *F16L 58/00*        (2006.01)
    *F16L 59/00*        (2006.01)
              (Continued)

(52) U.S. Cl.
    CPC .............. *F16L 58/00* (2013.01); *F16L 59/00* (2013.01); *F16L 59/07* (2013.01); *F16L 59/12* (2013.01);
              (Continued)

(58) Field of Classification Search
    CPC . F16L 58/00; F16L 59/14; F16L 59/07; F16L 59/12; F16L 59/00; G01N 17/04; G01N 33/0036
    See application file for complete search history.

(56) References Cited

U.S. PATENT DOCUMENTS 3,388,724 A     6/1968   Mowell
3,642,308 A   *   2/1972   Zeile, Jr. ............... F16L 59/143
                                        285/47
               (Continued)

FOREIGN PATENT DOCUMENTS

CN        105276303 A     1/2016
CN        106704768 A     5/2017
               (Continued)

OTHER PUBLICATIONS

Exam Report issued in Australian Application No. 2022407959, dated May 23, 2025.

(Continued)

*Primary Examiner* — Craig M Schneider
*Assistant Examiner* — Christopher D Ballman
(74) *Attorney, Agent, or Firm* — Andrus Intellectual Property Law, LLP

(57) ABSTRACT

A system and a method are for reducing a corrosive environment for a pipeline segment defined between a first end and a second end. The pipeline segment has a fluid pipe, a protective cover surrounding the fluid pipe and an annular space defined between the fluid pipe and the protective cover, the annular space being at least partly filled with an insulation material. The method has the steps of: providing an inlet at the first end for supplying a protective gas inside the annular space; providing a sensor at the second end of the pipeline segment; arranging a sensing element of the sensor inside the annular space for monitoring any corrosive environment therein; providing a protective gas source in (Continued)

fluid communication with the inlet; and controlling the supply of protective gas from the protective gas source based on signals from the sensor.

18 Claims, 3 Drawing Sheets

(51) Int. Cl.

| | | |
|---|---|---|
| *F16L 59/07* | (2006.01) |
| *F16L 59/12* | (2006.01) |
| *F16L 59/14* | (2006.01) |
| *G01N 17/04* | (2006.01) |
| *G01N 33/00* | (2006.01) |

(52) U.S. Cl.
CPC .............. *F16L 59/14* (2013.01); *G01N 17/04* (2013.01); *G01N 33/0036* (2013.01)

(56) References Cited

U.S. PATENT DOCUMENTS

| | | | | |
|---|---|---|---|---|
| 5,036,287 | A * | 7/1991 | Serwatzky | G01N 17/00 324/71.2 |
| 8,534,306 | B2 * | 9/2013 | Ayers | F16L 1/26 137/15.14 |
| 8,810,264 | B2 * | 8/2014 | Bohon | G01N 27/121 324/700 |
| 9,267,874 | B2 * | 2/2016 | Lorenz | G01N 17/00 |
| 10,481,099 | B2 * | 11/2019 | Yunker | G01N 21/81 |
| 10,982,508 | B2 * | 4/2021 | Rebello | F16L 55/18 |
| 11,137,361 | B2 * | 10/2021 | Karschnia | G01N 25/18 |
| 11,428,623 | B2 * | 8/2022 | Liu | G01N 17/04 |
| 2002/0083993 | A1 * | 7/2002 | Bohon | F16L 59/14 138/146 |
| 2005/0155663 | A1 | 7/2005 | Dhellemmes | |
| 2010/0319435 | A1 * | 12/2010 | Strong | G01M 3/002 324/700 |
| 2012/0056634 | A1 * | 3/2012 | Bohon | G01N 27/121 324/700 |
| 2020/0088663 | A1 * | 3/2020 | Karschnia | F16L 59/14 |

FOREIGN PATENT DOCUMENTS

| | | |
|---|---|---|
| CN | 111075999 A | 4/2020 |
| CN | 210566997 U | 5/2020 |

OTHER PUBLICATIONS

International Search Report and the Written Opinion for Corresponding International Application No. PCT/NO2022/050277, dated Feb. 28, 2023.

Search Report for Corresponding Norwegian Application No. 20211477, dated May 25, 2022.

Extended European Search Report for EP Application No. 22904736.0, dated Nov. 4, 2025.

Cao Qing et al: "A Review of Corrosion under Insulation: A Critical Issue in the Oil and Gas Industry", Metals 2022, vol. 12, No. 4. Published Mar. 25, 2022. https://doi.org/10.3390/met12040561.

* cited by examiner

METHOD AND A SYSTEM FOR REDUCING CORROSIVE ENVIRONMENT FOR A PIPELINE

CROSS-REFERENCE TO RELATED APPLICATIONS

This application is the U.S. national stage application of International Application No. PCT/NO2022/050277, filed Dec. 5, 2022, which international application was published on Jun. 15, 2023, as WO 2023/106925 in the English language. The International Application claims priority to Norwegian Patent Application No. 20211477, filed Dec. 8, 2021. The international application and Norwegian application are both incorporated herein by reference, in their entirety.

FIELD

The invention relates to a method and a system for reducing a corrosive environment for a pipeline segment being surrounded by insulation covered by a protective cover. More specifically, it relates to a method and a system for reducing the corrosive environment by supplying a protective gas between the pipeline segment and the protective cover.

BACKGROUND

In the chemical and the petrochemical industry, there is often a need for thermal insulating pipelines and other equipment, due to technical, economic, or environmental reasons. The thermal insulation reduces heat transfer between pipeline and the surroundings, in addition to protect the pipeline and the contents of the pipeline against heat from the surroundings, for example due to a fire. The thermal insulation is typically protected by a cladding surrounding the insulation.

Corrosion Under Insulation (CUI) is a major problem when insulating pipelines. CUI is a severe localized corrosion damage that is caused by moisture present on the external surface of insulated pipelines and equipment. The moisture may be due to condensation on the pipeline surface facing the insulation. The occurrence of condensation depends on the relative humidity of the air inside the insulation and temperature difference between the pipeline and the surroundings. The corrosion processes are well understood, but CUI often goes undetected until the damage is significant, which may lead to catastrophic failures like leaks, downtime, equipment failures or explosions. Thus, CUI represents both an increased maintenance costs and an increased safety risk.

The focus of the industry has typically been to monitor the humidity adjacent the surface of the pipeline and to detect moisture that may represent an increased risk of CUI. If moisture above a predetermined level is detected remedial actions are initiated. Different methods of CUI detection exist, such as visual inspection, infrared thermography, realtime radiography, computed radiography, digital detector array, ultrasonic thickness measurement, or pulsed eddy current.

When CUI has been detected, or there are reasons to believe that CUI may have occurred, there are high costs related to maintenance. When CUI is detected, a portion of the pipeline must usually be replaced, which is laborious and costly. Indeed, cost studies have shown that 40-60% of pipeline maintenance costs are caused by CUI, and that approximately 10% of the total maintenance budget is spent repairing damage from CUI.

If the insulated pipeline or equipment are protected from moisture and corrosion, instead of being monitored, the risk of CUI could decrease drastically. By inserting a protective gas such as an inert gas between the pipeline surface and the cladding, oxygen and moisture could be removed, and condensation and corrosion would likely not occur.

The document CN106704768 A describes a method wherein a protective sleeve around a gas pipeline is filled with an inert gas, preferably at a pressure between 0.15 to 0.2 MPa to prevent air entering the protective sleeve. This method requires a fluid tight system and cladding, which in practice is difficult to achieve. The gas may gradually leak out and be replaced by oxygen leaking in, and the risk of corrosion would increase again.

The document US 2005/0155663 A1 discloses a thermally insulated pipeline for transportation of liquefied natural gas. The insulated pipeline comprising from the inside to the outside: a first sealed pipe, a first thermal insulation layer made of insulating material, a second sealed pipe, a second thermal insulation layer made of insulating material, and a ballast made of material with a density above that of sea water. The pipeline additionally comprising a sealed, impact-resistant protective casing outside said ballast. At least one of the first and second thermal insulation layer may be flushed with an inert gas circulating therethrough to prevent the formation of an explosive mixture caused by gas resulting from possible leak being brought into contact with air contained in the thermal insulation.

Publication CN 210566997 U discloses a water inlet pipe with anti-freezing function. The water inlet pipe comprises an inner tube and a metal sleeve surrounding the inner tube. The anti-freezing function is obtained by extracting air from an annulus defined between the inner tube and the sleeve, and injecting a heat insulating gas into the annulus until a predetermined pressure is achieved.

In view of the above-described problems there is a need to further develop a method for preventing CUI.

SUMMARY

The invention has for its object to remedy or to reduce at least one of the drawbacks of the prior art, or at least provide a useful alternative to prior art.

The object is achieved through features which are specified in the description below and in the claims that follow.

The invention is defined by the independent patent claims. The dependent claims define advantageous embodiments of the invention.

In a first aspect the invention relates to a method for reducing a corrosive environment for a pipeline segment defined between a first end and a second end. The pipeline segment comprises a fluid pipe, a protective cover surrounding the fluid pipe, and an annular space defined between the fluid pipe and the protective cover. The annular space is at least partly filled with an insulation material. The method comprises the steps of:

providing an inlet at the first end for supplying a protective gas into the annular space;

providing a sensor at the second end of the pipeline segment;

arranging a sensing element of the sensor inside the annular space for monitoring any corrosive environment therein;

providing a protective gas source in fluid communication
with the inlet; and controlling the supply of protective gas from the protective gas source based on signals from the sensor.

The effects of the features of the method in accordance with the invention are as follows. First of all, a key feature of the method is to provide the protective gas source in fluid communication with the inlet for supplying the protective gas between the fluid pipe and the protective cover, that is inside the annular space. The protective gas at least reduces oxygen and moisture from the annular space and therefore reducing the possibility for corrosion on the fluid pipe. The protective gas source may be connected to the inlet as long as the fluid pipe is in use and the protective gas source may therefore ensure that the annular space between the fluid pipe and the protective cover is always filled with protective gas. This bypasses the problem of keeping the protective cover completely fluid tight. As the protective gas leaks out from the protective cover, for example at pipe connections such as flanges, the protective gas source refills the annular space of the pipeline segment with protective gas. Secondly, the sensor monitoring any corrosive environment inside the annular space, can detect if this volume should be refilled with protective gas or if the amount of protective gas is sufficient. The sensor is positioned at the second end of the pipeline segment so that it monitors the volume furthest away from the inlet. If the second end is sufficiently filled with the protective gas, the volume between the first and the second end of the pipeline segment is also sufficiently filled with protective gas. The signals sent from the sensor determine if the supply of protective gas should be increased, kept constant or paused. The sensor may send a signal if the measured parameter deviates from a predetermined threshold or interval. Lastly, supplying the pipeline segment with the protective gas may be advantageous for reducing noise from the pipeline segment to the surroundings. The protective gas may also act as a flame retardant as the oxygen is at least reduced from the volume around the fluid pipe. The method is easily implemented with existing insulated pipelines.

The invention is also suitable for other insulated equipment, such as valves, process columns and tanks, as would be acknowledged by a person skilled in the art.

In order to facilitate understanding of the invention one or more expressions are further defined hereinafter.

The wording "annular space" must be interpreted as the annulus between the outer surface of the fluid pipe and the inner surface of the protective cover. The annular space is filled, completely or partially, with an insulating material.

The wording "filled with protective gas" must be interpreted as filled with a sufficient amount of protective gas. The sufficient amount of protective gas may be 95%.

In an embodiment of the method according to the invention, the method may comprise arranging the sensing element of the sensor closer to the fluid pipe than the protective cover. Since the method aims at reducing the risk of corrosion of the fluid pipe by reducing the corrosive environment surrounding the fluid pipe, it could be an advantage to monitor the corrosive environment close to the fluid pipe.

In an embodiment of the method according to the invention, the method may further comprise providing at least one protective gas distribution tube inside the annular space, along at least a portion of the pipeline segment, the at least one tube being provided with perforations and being in fluid communication with the inlet. The perforations may be positioned with equal distance between each other. The tube may especially be advantageous if the annular space is completely filled with an insulating material. The insulating material may increase the time it takes for the protective gas to reach the second end of the pipeline segment. The at least one tube ensures an even distribution of the protective gas along the pipeline segment, all the way to the end of the tube.

The at least one tube may be arranged closer to the fluid pipe than the protective cover. It may be advantageous to ensure that the protective gas is distributed close to the fluid pipe to prevent corrosion on the surface of the fluid pipe.

The method may further comprise providing at least one further sensor between the first end and the second end of the pipeline segment and arranging a sensing element of the at least one further sensor inside the annular space, for monitoring any corrosive environment therein. It may be advantageous to have more than one sensor along the pipeline segment to collect more data on the corrosive environment inside the annular space. The sensors may be distributed equally along the pipeline segment or be positioned at locations of the pipeline segment where the risk for CUI may be higher.

In a second aspect the invention relates to a system for reducing a corrosive environment for a pipeline segment defined between a first end and a second end. The pipeline segment comprises a fluid pipe, a protective cover surrounding the fluid pipe, and an annular space defined between the fluid pipe and the protective cover. The annular space is at least partly filled with an insulation material. The system comprises:

a protective gas source;

an inlet in fluid communication with the protective gas source, the inlet being positioned at the first end of the pipeline segment for supplying a protective gas from the protective gas source inside the annular space;

a sensor positioned at the second end of the pipeline segment, wherein a sensing element of the sensor is arranged inside the annular space for monitoring any corrosive environment therein;

a control unit for receiving signals from the sensor and controlling the supply of protective gas from the protective gas source based on the signals.

In an embodiment of the system according to the invention, the sensing element of the sensor is arranged closer to the fluid pipe than the protective cover.

In a further embodiment of the system in accordance with the invention, the system may further comprise at least one protective gas distribution tube provided inside the annular space, along at least a portion of the pipeline segment. The at least one tube may be provided with perforations and being in fluid communication with the inlet.

The at least one tube may be arranged closer to the fluid pipe than the protective cover.

The system may further comprise at least one further sensor arranged between the first end and the second end of the pipeline segment. A sensing element of the at least one further sensor may be arranged inside the annular space for monitoring any corrosive environment therein.

BRIEF DESCRIPTION OF THE DRAWINGS

In the following is described examples of embodiments illustrated in the accompanying figures, wherein.

DETAILED DESCRIPTION OF THE DRAWINGS

Figure 1:
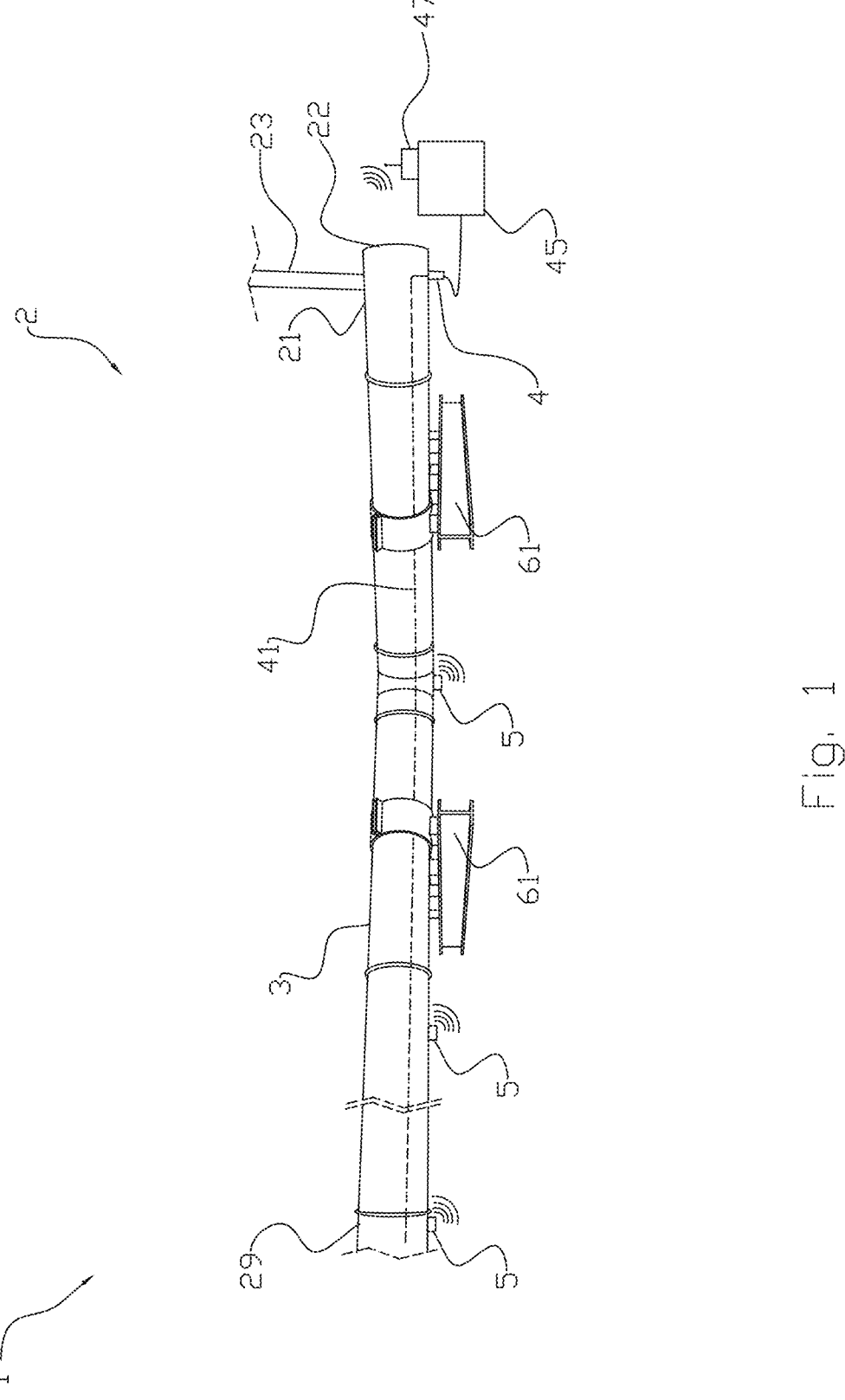
FIG. 1 shows a perspective view of an embodiment of the system according to the second aspect of the invention.

Any positional indications refer to the position shown in the figures.

In the figures, same or corresponding elements are indicated by same reference numerals. For clarity reasons, some elements may in some of the figures be without reference numerals.

A person skilled in the art will understand that the figures are just principal drawings. The relative proportions of individual elements may also be distorted.

In the figures, reference number 2 denotes a pipeline segment defined between a first end 21 and a second end 29. Further, reference number 1 denotes a system for reducing a corrosive environment for the pipeline segment 2. The pipeline segment 2 comprises a fluid pipe 20, a protective cover 3, which is surrounding the fluid pipe 20. An annular space 35 is defined between the fluid pipe 20 and the protective cover 3. The annular space 35 is at least partly filled with an insulating material 37. The system 1 comprises a protective gas source 45 and an inlet 4 in fluid communication with the protective gas source 45. The inlet 4 is positioned at the first end 21 of the pipeline segment 2 for supplying a protective gas (not shown) from the protective gas source 45 inside the annular space 35. Furthermore, a sensor 5 is positioned at the second end 29 of the pipeline segment 2. The sensor 5 comprises a sensing element 51, which is arranged inside the annular space 35 for monitoring any corrosive environment inside the annular space 35.

FIG. 1 shows the pipeline segment 2 with a first end 21 and a second end 29. The first end can typically be at an end cap 22 of a pipeline. The fluid pipe 20 is in fluid communication with a pipeline inlet 23 positioned at the first end 21. The pipeline segment 2 is supported by supportive elements 61, here shown as beams arranged on a ground. The first and the second end of a pipeline segment may typically be at positions on the pipeline where valves and/or other equipment are connected.

Although not shown in FIG. 1, it should be clear that the insulated pipeline segment 2 may comprise auxiliary equipment such as for example insulated valves forming part of the pipeline.

The pipeline segment 2, from which a corrosive environment is at least reduced according to the invention, can be around 100 meters in length. The pipeline segment 2 may be shorter or longer than 100 meters.

The protective gas from the protective gas source 45 travels through the inlet 4 at the first end 21 and through a protective gas distribution tube 41 arranged along at the pipeline segment 2, inside the annular space 35. The tube 41 is provided with perforations with a mutual distance between the perforations. The protective gas is in this way distributed inside the annular space along the pipeline segment 2 through the perforations. The distances between the perforations may be equal along a part of the tube 41, or they may be unequal along a part of the tube 41.

The protective gas supplied to the pipeline segment 2 may be an inert gas, preferably nitrogen because of its availability and low cost. An inert gas, such as nitrogen, is effective in reducing moisture and oxygen from the annular space 35 and reduces in this way the possibility for corrosion on the pipeline segment 2.

The pipeline segment 2 is provided with a sensor 5 arranged on the protective cover 3 at the second end 29 of the pipeline segment 2, in addition to further sensors 5 (two shown) between the first 21 and the second end 29, for monitoring any corrosive environment within the annular space 35. The sensors 5 may monitor the oxygen level, or the level of the protective gas, such as a nitrogen sensor, or they may be moisture sensors. The sensor 5 at the second end 29 may be important to ensure that the protective gas fills the whole length of the pipeline segment 2 between the first 21 and the second end 29. The further sensors 5 between the first end 21 and the second end 29 may be arranged at positions where the likelihood for corrosion may be higher, for example due to curves in the fluid pipe 20.

The sensors 5 is configured for issuing signals to a control unit 47 (FIG. 1) which, upon receiving the signals, controls the supply of protective gas from the protective gas source 45 to the annular space 35 through the inlet 4. The sensor 5 may issue a signal when the measured parameter deviates from a predetermined interval of values. It may be advantageous that the level of oxygen within the annular space 35 remains below for example 5%. The sensors 5 may typically be configured for sending signals to the control unit 47. The control unit 47 may typically be configured to increase, decrease, or pause the supply of protective gas from the protective gas source 45, based on the received signals. For example, if the oxygen level is measured by an oxygen sensor to be above 5%, or the nitrogen level is measured by a nitrogen sensor to be below 95%, the signal from the sensor 5 activates the protective gas source to increase of the protective gas supply to the annular space 35. If the oxygen level is between 5% and 3%, or the nitrogen level is between 95% and 97%, for example, the rate of protective gas supply may be held constant. If the oxygen level is below 3%, or the nitrogen level is above 97%, for example, the protective gas supply may be paused. If a moisture sensor detects moisture within the annular space 35, the supply of protective gas may be increased. Other appropriate sensors and predetermined threshold values and intervals may be used.

In another example the sensors 5 is configured for sending information about the measured value to the control unit at predetermined intervals. The information is interpreted by the control unit 47, which then controls the rate of protective gas supply based on the information received.

Different types of sensors may be used in combination. The signals may be sent wireless or through a wire.

Figure 2:
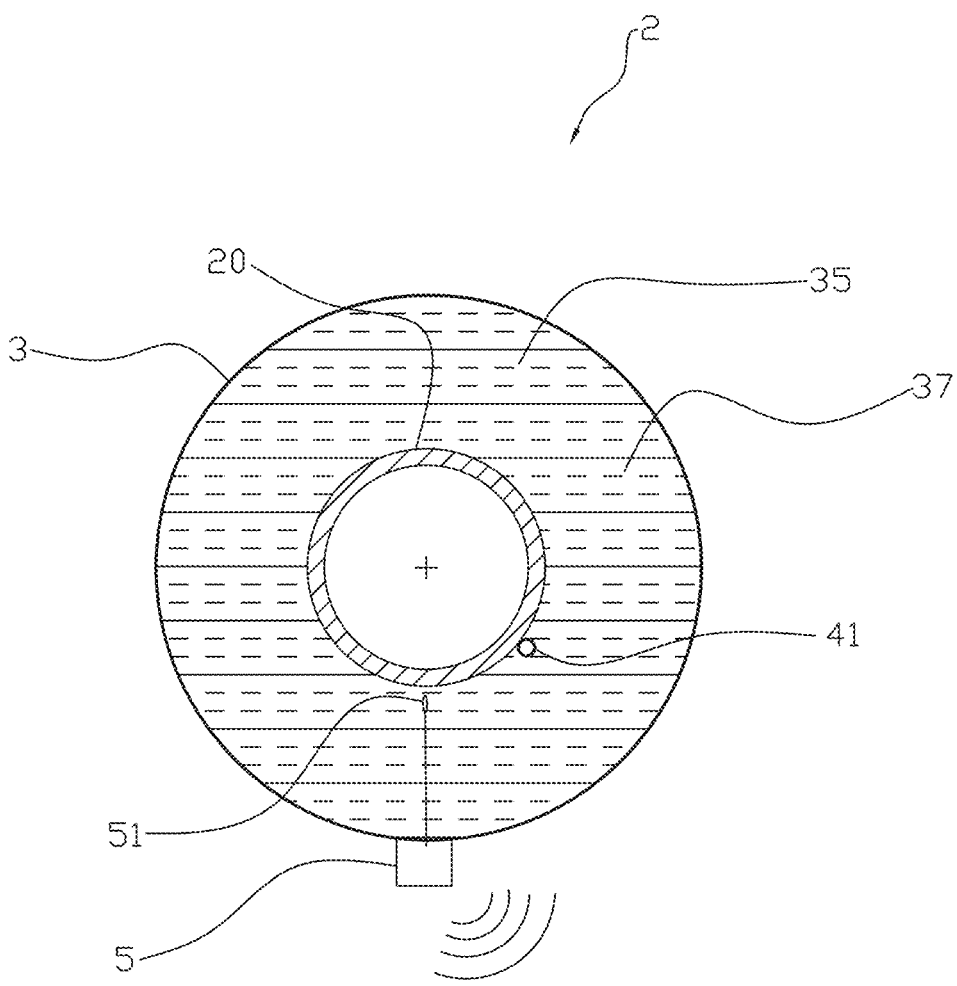
FIG. 2 shows a cross section of an embodiment of a pipeline segment according to the second aspect of the invention.

Referring now to FIG. 2, which shows a cross section of a pipeline segment 2 where the annular space 35 between the fluid pipe 20 and the protective cover 3 is fully filled with an insulating material 37. The insulating material 37 may slow down or restrict the distribution of the protective gas along the pipeline segment 2 and thereby reduce the effect of the invention. To at least mitigate such a reduced effect, it may be advantageous to use a protective gas distribution tube 41 to ensure that the protective gas from the protective gas source 45 is distributed inside the annular space 35, so that the pipeline segment 2 is filled with protective gas.

In the example shown in FIG. 2, the tube 41 is arranged close to the fluid pipe 20. It may be advantageous to ensure that the protective gas is distributed close to the fluid pipe 20 to prevent corrosion on the surface of the fluid pipe 20. The tube 41 may be arranged anywhere within the annular space 35. It should be noted that more than the one tube 41 may be arranged spaced-apart along the pipeline segment 2.

Figure 3:
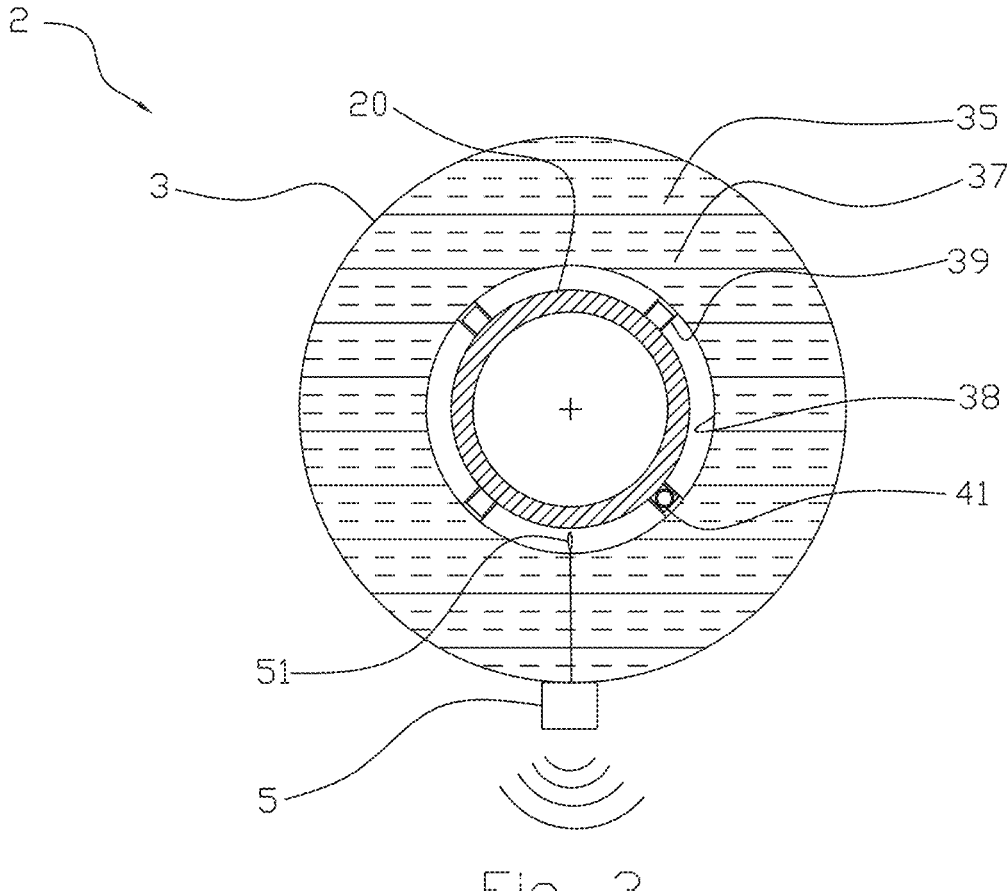
FIG. 3 shows a cross section of another embodiment of a pipeline segment according to the second aspect of the invention.

FIG. 3 shows a cross section of a pipeline segment 2 where the annular space 35 is partially filled with insulating material 37. Spacers 39 are arranged along the periphery of the fluid pipe 20, and along the length of the pipeline segment 2 between the first end 21 and the second end 29 to prevent the insulating material 37 from abutting against the fluid pipe 20. An annulus 38 is defined between the insulation material 37 and the fluid pipe 20. In the example shown in FIG. 3, the protective gas distribution tube 41 is positioned within the annulus 38, arranged inside the spacers 39. This may be advantageous as the tube 41 can easily be thread through the spacers 39 upon installation and may require no further attachment. The tube 41 may also be arranged within the annulus 38, outside of the spacers 41. The tube 41 may alternatively or additionally be arranged within the insulation material 37.

In another embodiment of the invention (not shown), more than one protective gas distribution tubes 41 are arranged along at the pipeline segment 2, inside the annular space 35, for distribution of the protective gas along the pipeline segment 2.

Figure 4:
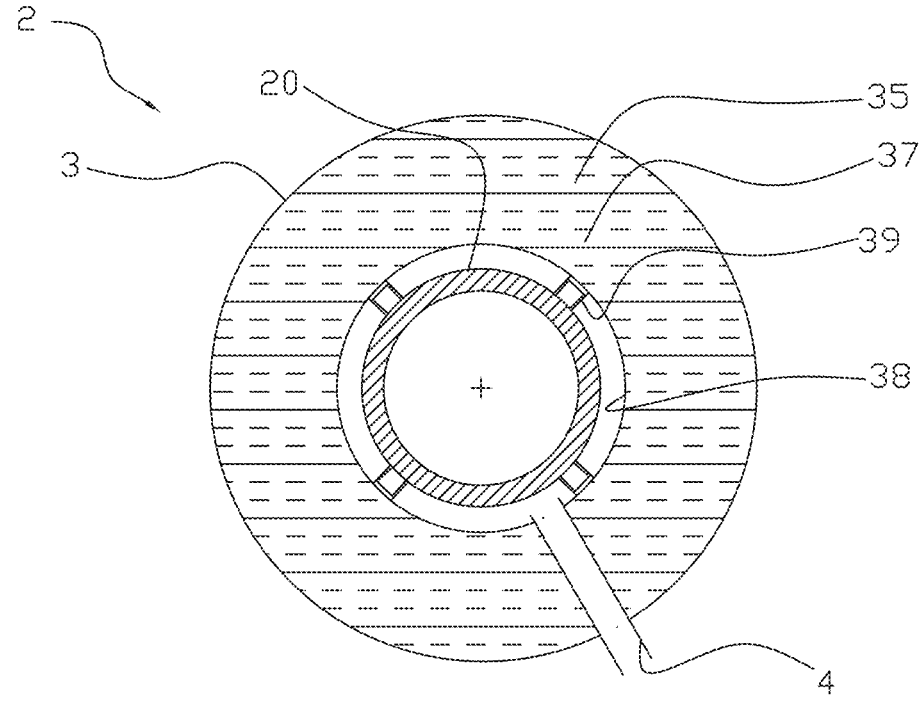
FIG. 4 shows a cross section of yet another embodiment of a pipeline segment according to the second aspect of the invention.

FIG. 4 shows another example wherein the protective gas distribution tube 41 is omitted. The inlet 4 passes through the insulation material 37, for supplying protective gas into the annulus 38. The protective gas may distribute quicker along the pipeline segment 2 within the annulus 38, than within the insulating material 37. The inlet 4 may in other embodiments supply the protective gas within the insulation material 37.

In the examples shown in FIGS. 2 and 3, the sensing element 51 of the sensor 5 is arranged close to the surface of the fluid pipe 20. It may be advantageous to monitor the environment close to the fluid pipe 20 to ensure that the volume close to the fluid pipe 20 is filled with the protective gas.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage. The invention may be implemented by means of hardware comprising several distinct elements, and by means of a suitably programmed computer. In the device claims enumerating several means, several of these means may be embodied by one and the same item of hardware.

The invention claimed is:

1. A method for reducing a corrosive environment for a pipeline segment defined between a first end and a second end, the pipeline segment comprising a fluid pipe, a protective cover surrounding the fluid pipe, and an annular space defined between the fluid pipe and the protective cover, the annular space being at least partly filled with an insulation material, the method comprising the steps of:

providing an inlet at the first end for supplying a protective gas into the annular space;

providing a sensor at the second end of the pipeline segment;

arranging a sensing element of the sensor inside the annular space for monitoring any corrosive environment therein;

providing a protective gas source in fluid communication with the inlet; and controlling the supply of protective gas from the protective gas source based on signals from the sensor.

2. The method according to claim 1, further comprising arranging the sensing element of the sensor closer to the fluid pipe than the protective cover.

3. The method according to claim 2, further comprising providing at least one protective gas distribution tube inside the annular space, along at least a portion of the pipeline segment, the at least one protective gas distribution tube being provided with perforations and being in fluid communication with the inlet.

4. The method according to claim 2, further comprising providing at least one further sensor between the first end and the second end of the pipeline segment and arranging a sensing element of the at least one further sensor inside the annular space, for monitoring any corrosive environment therein.

5. The method according to claim 1, further comprising providing at least one protective gas distribution tube inside the annular space, along at least a portion of the pipeline segment, the at least one protective gas distribution tube being provided with perforations and being in fluid communication with the inlet.

6. The method according to claim 5, further comprising arranging the at least one protective gas distribution tube closer to the fluid pipe than the protective cover.

7. The method according to claim 6, further comprising providing at least one further sensor between the first end and the second end of the pipeline segment and arranging a sensing element of the at least one further sensor inside the annular space, for monitoring any corrosive environment therein.

8. The method according to claim 5, further comprising providing at least one further sensor between the first end and the second end of the pipeline segment and arranging a sensing element of the at least one further sensor inside the annular space, for monitoring any corrosive environment therein.

9. The method according to claim 1, further comprising providing at least one further sensor between the first end and the second end of the pipeline segment and arranging a sensing element of the at least one further sensor inside the annular space, for monitoring any corrosive environment therein.

10. A system for reducing a corrosive environment for a pipeline segment defined between a first end and a second end, the pipeline segment comprising a fluid pipe, a protective cover surrounding the fluid pipe, and an annular space defined between the fluid pipe and the protective cover, the annular space being at least partly filled with an insulation material, the system comprises:

a protective gas source;

an inlet in fluid communication with the protective gas source, the inlet being positioned at the first end of the pipeline segment for supplying a protective gas from the protective gas source into the annular space, characterized in that the system further comprises:

a sensor positioned at the second end of the pipeline segment, wherein a sensing element of the sensor is arranged inside the annular space for monitoring any corrosive environment therein;

a control unit for receiving signals from the sensor and controlling the supply of protective gas from the protective gas source based on the signals.

11. The system according to claim 10, wherein the sensing element of the sensor is arranged closer to the fluid pipe than the protective cover.

12. The system according to claim 11, further comprising at least one protective gas distribution tube provided inside the annular space, along at least a portion of the pipeline segment, the at least one protective gas distribution tube being provided with perforations and being in fluid communication with the inlet.

13. The system according to claim 11, further comprising at least one further sensor arranged between the first end and the second end of the pipeline segment, wherein a sensing element of the at least one further sensor is arranged inside the annular space for monitoring any corrosive environment therein.

14. The system according to claim 10, further comprising at least one protective gas distribution tube provided inside the annular space, along at least a portion of the pipeline segment, the at least one protective gas distribution tube being provided with perforations and being in fluid communication with the inlet.

15. The system according to claim 14, wherein the at least one protective gas distribution tube is arranged closer to the fluid pipe than the protective cover.

16. The system according to claim 15, further comprising at least one further sensor arranged between the first end and the second end of the pipeline segment, wherein a sensing element of the at least one further sensor is arranged inside the annular space for monitoring any corrosive environment therein.

17. The system according to claim 14, further comprising at least one further sensor arranged between the first end and the second end of the pipeline segment, wherein a sensing element of the at least one further sensor is arranged inside the annular space for monitoring any corrosive environment therein.

18. The system according to claim 10, further comprising at least one further sensor arranged between the first end and the second end of the pipeline segment, wherein a sensing element of the at least one further sensor is arranged inside the annular space for monitoring any corrosive environment therein.

* * * * *